United States Patent
Cavazza

(12) 
(10) Patent No.: US 6,429,230 B1
(45) Date of Patent: *Aug. 6, 2002

(54) TREATING CHRONIC UREMIC PATIENTS UNDERGOING PERIODICAL DIALYSIS

(75) Inventor: Claudio Cavazza, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/971,076

(22) Filed: Oct. 5, 2001

Related U.S. Application Data

(63) Continuation-in-part of application No. 09/761,639, filed on Jan. 18, 2001, now Pat. No. 6,335,369.
(60) Provisional application No. 60/176,626, filed on Jan. 19, 2000, and provisional application No. 60/186,328, filed on Mar. 2, 2000.

(51) Int. Cl.$^7$ ................................................ A01N 37/12
(52) U.S. Cl. ...................................................... 514/561
(58) Field of Search ......................................... 514/561

(56) References Cited

U.S. PATENT DOCUMENTS

| | | | |
|---|---|---|---|
| 4,237,167 A | * 12/1980 | Cavaza | |
| 4,272,549 A | * 6/1981 | Cavazza | ..................... 424/316 |
| 4,602,039 A | * 7/1986 | Cavazza | ..................... 514/561 |
| 6,051,608 A | * 4/2000 | Santaniello et al. | ........ 514/556 |
| 6,245,378 B1 | * 6/2001 | Cavazza | ..................... 426/656 |

FOREIGN PATENT DOCUMENTS

WO    WO 99 07419 A    *  2/1999

OTHER PUBLICATIONS

Ahmad et al Kidney International, vol. 36, Suppl.27 (1989), pp. S–243–S–246 Fatty Acid abnormalities in hemodialysis patients: Effect of L–carnitine administration.

Golper et al Kidney International vol. 38 (1990) pp. 904–911 Multicenter trial of L–carnitine in maintenance hemodialysis patients. I. Carnitine concentrations and lipid effects.

Ahmad et al Kidney International vol. 38 (1990) pp. 912–918 Multicenter trial of L–carnitine in maintenance hemodialysis patients. II. Clinical and biochemical effects.

Borum P.R. and Taggart E.M., "Carnitine Nutriture of Dialysis Patients", *J. Am. Diet. Assoc.* 86:644–647 (1986).

Bazzato G. et al, "Myasthenia –Like Syndron After D.L–But not L Carnitine", Lacneet 1:1209 (1981).

Kavucu S. et al, "The Effects of L–Carnitine on Respiratory Function Tests in Children Undergoing Chronic Hemodialysis", *Turk. J. Pedia.* 40(1):79–84 (1998).

Thomas, S. et al., "Effects of L–Carnitine on Leukocyte Function and Viability in Hemodialysis Patients: ADouble–Blind Randomized Trial", *Am. J. Kidney Dis.*, 34(4):678–687 (1999).*

Elisaf, M. et al., "Effect of L–Carnitine Supplementation on Lipid Parameters in Hemodialysis Patients", *Am. J. Nephrol.* 18(5):416–421 (1998).*

Topaloğlu R. et al, "Effect of Carnitine Supplementation on Cardiac Function in Hemodialyzed Children," *Acta. Paediatr Jpn* 40:26–29 (1998).*

Vacha, G.M. et al, "*L*–Carnitine Addition to Dialysis Fluid", *Nephron* 51:237–242 (1989).*

Fiorini, F. et al. "Carnitine metalbolism in chronic kidney failure", Clinica Terapeutica (1992 Jan.) 140 (1 PT 2) 31–4 XP000999033.*

Khoss, A.E. et al, "'L.carnitine therapy and myocardial function in children treated with chronic hemodialysis", Wiener Klinische Wochenschrift (Jan. 6, 1989) 101 (1) 17–20; XP000996714.*

Huissoon, AP. et al, "Carnitine replacement and maintanance by addition of L–carnitine to dialysis fluid," Journal of Nephrology (1993) 6/2 (103–107); XP000996156.*

Wanner C., et al "Ketogenic and antiketogenic effects of L–carnitine in hemodialysis patients", Kidney International, Supplement (1989 Nov) 27 S264–8, XP000996144.*

* cited by examiner

*Primary Examiner*—James H. Reamer
(74) *Attorney, Agent, or Firm*—Nixon & Vanderhye

(57) ABSTRACT

The method for the treatment chronic uremic patients undergoing periodical dialysis is useful for preventing and/or treating carnitine deficiency in patients with end stage renal disease who are undergoing dialysis. The method according to the present invention comprises administering an effective dose of carnitine intravenously into the venous return line after each dialysis session.

16 Claims, 5 Drawing Sheets

TREATING CHRONIC UREMIC PATIENTS UNDERGOING PERIODICAL DIALYSIS

This application claims the benefit of Provisional Application No. 60/176,626, filed Jan. 19, 2000 and No. 60/186,328 filed Mar. 2, 2000, the entire content of which is hereby incorporated by reference in this application This application is a continuation-in-part of application Ser. No. 09/761,639, filed Jan. 18, 2001, now U.S. Pat. No. 6,334,369 the entire content of which is hereby incorporated by reference in this application.

The present invention relates to an improved therapeutic method for the treatment of chronic uremic patients undergoing periodical dialysis.

BACKGROUND OF THE INVENTION

It is well known that patients affected by chronic uraemia, undergoing periodic dialysis, frequently develop a clinical picture characterized by marked muscular asthenia and a sensation of torpor, particularly evident immediately following dialysis and which may often last even for several hours making difficult, if not impossible, to resume working activity until these conditions subside. Clinical experts recognize this problem as "post-dialytic syndrome".

These conditions have been sometimes attributed to the loss of carnitine during dialysis.

A method for treating the post-dialytic syndrome by compensating for the loss of carnitine occurring during the dialysis session is disclosed in U.S. Pat. No. 4,272,549. This patent describes a method for alleviating asthenia and muscle weakness in a chronic uremic patient under regular dialysis treatment by administering to the patient a polysaline dialytic solution which contains a quantity of carnitine (this refers to L-carnitine throughout the present specification), or a pharmaceutically acceptable salt of it, sufficient to adjust the molar concentration of carnitine in the dialysis solution at least equal to the molar concentration of carnitine in the patient's plasma. Preferably, the concentration of carnitine in the dialytic solution is substantially equimolar to the concentration of carnitine in the patient's plasma, but a certain excess of carnitine is also provided, for example between 50 and 100 $\mu$mole per liter of solution. A specific illustration includes administration of from 3 to 6 grams of carnitine or an equivalent amount of a pharmaceutically acceptable salt thereof. The carnitine may be administered orally, preferably on days between haemodialysis in amounts ranging from 3 to 6 grams of carnitine per day.

This oral treatment is coupled with a rather complex treatment regimen with carnitine during the dialytic session, in which carnitine is administered by slow infusion. On the days of dialysis, carnitine may also be administered partly by the oral route and partly by slow infusion. In this case, the overall quantity of carnitine administered shall not exceed approximately 10 g per day. "Slow infusion" means an infusion in which the solution containing carnitine, or any of its pharmaceutically acceptable salts, is administered at the rate of 20 to 40 drops per minute. Particularly favourable therapeutic results are said to be achieved by orally administering carnitine to the patient receiving dialysis treatment only on those days during which the patient does not receive dialysis, while during the actual dialytic session, a dialyzing liquid containing carnitine is used.

A preferred regimen for treating chronic uremic patients undergoing haemodialysis, includes the following steps:

1) on the days between one haemodialytic session and the next, oral administration to these patients of 3 to 6 g per day of carnitine or any of its pharmaceutically acceptable salts;

2) on the days of haemodialytic session, dialyzing these patients using, as dialyzing liquid, a solution containing a quantity of carnitine or of any of its pharmaceutically acceptable salts, sufficient to adjust the molar concentration of carnitine in the dialysis solution at least equal to the molar concentration of the plasma carnitine of the patient receiving dialytic treatment.

Using this procedure, it is possible to avoid the loss of plasma carnitine which otherwise takes place during a haemodialytic session; that is, the concentration of plasma carnitine remains practically unchanged during the dialytic session. In this manner, it is possible to avoid tissue carnitine depletion, which is the long-term consequence of repeated losses of carnitine the patient undergoes during successive dialytic sessions over a prolonged period of time, for example a month or longer.

Although the desired objective is achieved using a hemodialysis solution equimolar in carnitine with respect to the patient's blood, it is preferred to operate with a slightly more concentrated solution. In practice, the haemodialysis solution contains 50 to 100, preferably 60–80 $\mu$moles/liter of carnitine or of any of its pharmaceutically acceptable salts. On the days of haemodialysis, carnitine may also be administered partly by the oral route and partly by slow infusion. In this case, the overall quantity of carnitine administered shall not exceed approximately 10 g per day.

The procedures in U.S. Pat. No. 4,272,549 are effective in treating "post-dialysis syndrome", but present a cumbersome schedule of treatment. This fact leads to problems. Patient compliance, whose quality of life is already heavily affected, is a concern as patients are apt to overlook the oral self-administration of a prescribed dosage of carnitine between the dialytic sessions. There is also the problem of carnitine bioavailability through the oral route, which is subject to saturation mechanism and to some restrictions as to the absorption sites (Harper at al. Eur. J. Clin. Pharmacol. 1988; 35(5):555–62 and Matsuda et al. Biol. Pharm. Bull July, 1998, 21 (7):752–5). Also, oral administration of carnitine to a chronic uremic patient may give rise to the accumulation of toxic metabolites.

A recent article by Sloan et al. (Am. J. Kidney Dis. August, 1998, 32(2):265–72) demonstrated that oral supplementation of carnitine is effective in improving the quality of life of patients in the early stage of treatment, but the perceived effect was not sustained through long term treatment (six months).

Other than the fact that carnitine deficiency may be connected with post-dialytic syndrome, this deficiency is a disturbance of the homeostasis of such an important inborn substance, that the medical community recognizes the necessity to treat carnitine deficiency per se.

SUMMARY OF THE INVENTION

Disclosed is a method for treating chronic uremic patients undergoing periodical dialysis. This method prevents and treats carnitine deficiency in patients with end stage renal disease who are undergoing dialysis. The method comprises administering to the dialysis patient an effective dose of carnitine intravenously into the venous return line at the conclusion of each dialysis session. Dialysis session as used herein means both haemodialysis and peritoneal dialysis.

The method of the present invention provides a surprising improvement over the procedures described in U.S. Pat. No. 4,272,549 and eliminates the need for oral treatment, without affecting the maintenance or correction of carnitine deficiency obtained by the administration of carnitine through intravenous route.

Ahmad S. et al (Kidney International, Vol. 36, Suppl. 27 (1989), S-243–S-246) report a study on the administration of L-carnitine in hemodialysis patients investigating the effect on fatty acid abnormalities in the patients' serum. Carnitine was given intravenously for the first six months at the dosage of 20 mg/kg and subsequently was reduced to 10 mg/kg. The administration was performed via the blood line after each dialysis session during the rinse back cycle. Patients treated with carnitine had a partial correction of the abnormal fatty acid profile noted in untreated dialysis patients. The authors found difficult to explain the persistence of some abnormalities in lipid profiles and made no effort to correlate plasma levels with possible clinical manifestations of fatty acid deficiency. This study is not related to the general picture of carnitine deficiency.

In two subsequent articles, Ahmad, Golper et al. (Kidney International, Vol. 38 (1990), 904–911 and 912–918) report a multicenter trial of carnitine in maintenance hemodialysis patients. The administration of carnitine was performed as described in the 1989 article, but, as a clinically significant study, the carnitine dose was kept constant at 20 mg/kg. In the first paper, the authors still investigate on the effect of carnitine on serum lipid profile, concluding that carnitine does not seem to have a great lipid-lowering potential. In the second paper, carnitine appears to be associated with a decrease in dialytic symptoms, an improvement in exercise capability, sense of well being. The skilled reader will observe that in the clinical trial no reduction of carnitine dosage was attempted or devised.

As it will be apparent from the detailed description below, the best mode of carrying out this invention provides an advantageous treatment wherein, after a starting dose of carnitine, which may also be intended as attack does, a lower maintenance dose is given.

The invention shall be disclosed in detail, with reference to Figures and Examples.

DETAILED DISCLOSURE OF THE INVENTION

Figure 1:
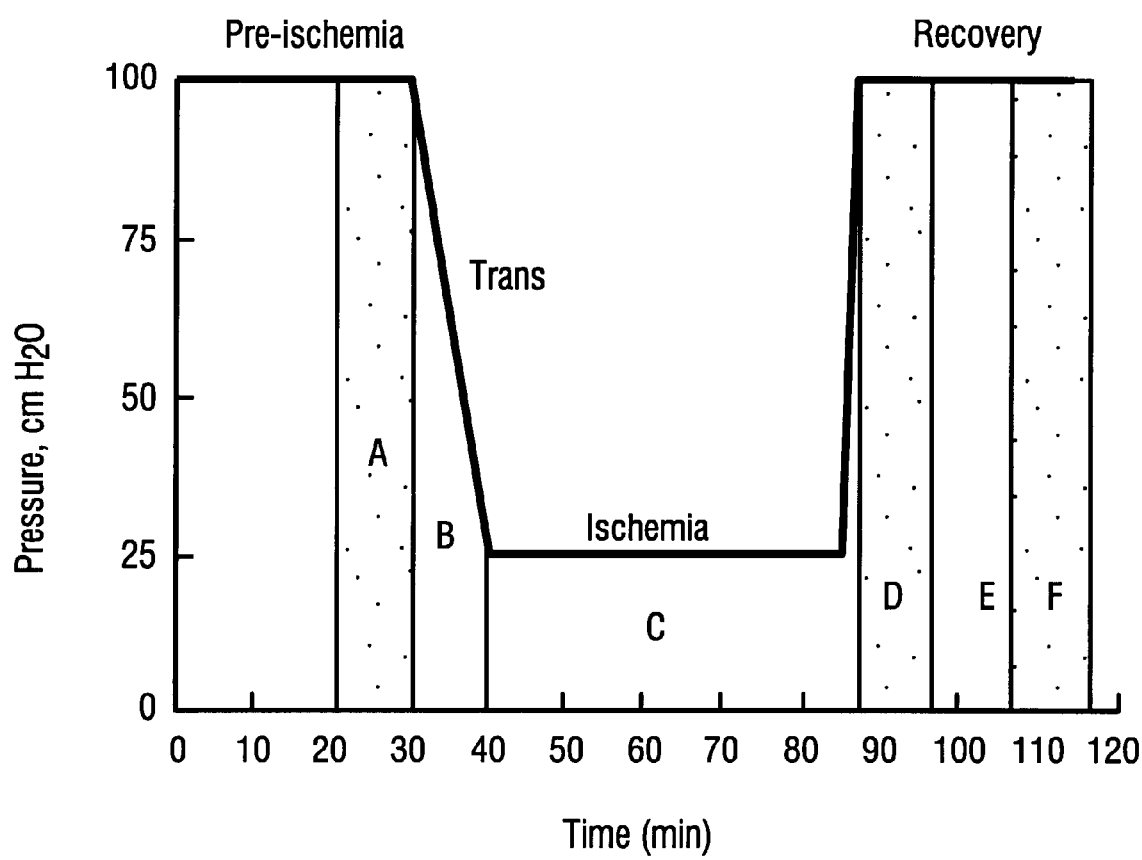
FIG. 1 illustrates a treatment schedule, where the letters A–F denote the heart effluent sampling times for the measurement of metabolites.

Disclosed are methods of preventing or treating carnitine deficiency in chronic uremic patients undergoing periodic dialysis by administering to the patient at the conclusion of dialysis an effective amount of L-carnitine, either as inner salt or a pharmaceutically acceptable salt thereof, preferably the salt is L-carnitine fumarate. Administration is by the intravenous route or by peritoneal route. Preferably from about 10 to about 20 mg/kg body weight of carnitine, calculated as L-carnitine, is administered into a venous return line at the conclusion of each dialysis session.

Also disclosed are methods of preventing carnitine deficiency in end stage uremic patients undergoing periodic dialysis over an extended period of time by administering to these patients at the conclusion of each dialysis session an effective amount of L-carnitine, either as inner salt or a pharmaceutically acceptable salt thereof.

The preferred starting dose is 10–20 mg/kg dry body weight administered as a slow 2–3 minute bolus injection into the venous return line after each dialysis session.

Initiation of the therapy may be prompted by through (pre-dialysis) plasma carnitine concentrations that are below normal (40–50 $\mu$mol/L). Dose adjustments should be guided by through (pre-dialysis) carnitine concentrations, and downward dose adjustments (for example to 5 mg/kg after dialysis) may be made as early as the third or fourth week of therapy.

Carnitine can be administered as inner salt or in any pharmaceutically acceptable salts thereof.

Examples of pharmaceutically acceptable salts are disclosed in U.S. Pat. Nos. 6,124,360, 6,130,249, 6,080,786 4,602,039 application No. WO98/44918, and an exemplary list is given in WO00/06134.

The procedures described in U.S. Pat. No. 4,272,549 discussed above are not specific to any particular carnitine salt. In the present invention for treating chronic uremic patients undergoing periodical dialysis, any of the pharmaceutically acceptable salts of carnitine are acceptable. However, at times the skilled clinician may encounter problems with some patients. During the dialytic session, some patients are affected by hypervolemic heart, and this can give a severe outcome as heart failure. Moreover, a number of patients undergoing hemodialysis are affected by diabetes.

In a particular embodiment of the present invention, it has been found that fumarate of L-carnitine exerts a surprising beneficial effect on heart. Moreover, due to its physiologic role, fumarate may have beneficial effects in diabetic patients. Accordingly, a particular embodiment of the present invention relates to the method above disclosed, wherein fumarate is the pharmaceutically acceptable salt of L-carnitine.

Suitable formulations of carnitine, or a pharmaceutically acceptable salt thereof, are in the form of injectable compositions, for example comprising an equivalent amount of carnitine of 200 mg per 1 mL. A 2.5 or a 5 mL single dose ampoule may be convenient. When a pharmaceutically acceptable salt of L-carnitine is used, such as fumarate L-carnitine, the amount of active ingredient will be calculated so as to provide an equivalent amount of L-carnitine as above specified.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

DESCRIPTION OF THE PREFERRED EMBODIMENT

Patients showing a pre-dialysis carnitine level equal or lower than 40–50 $\mu$M were treated by the procedures of the present invention with a 10–20 mg/kg dose of carnitine at the conclusion of the 4-hours dialytic session. According to a standard dialytic schedule, the treatment was repeated twice a week every 44 hours, then after 68 hours. This treatment was continued for 3–4 weeks, monitoring pre-dialytic levels of carnitine. As a further embodiment of the present invention, a maintenance dosage is provided, administering, as a preferred example, a dose of 5 mg/kg of carnitine. The maintenance dosage may be practised with the same schedule detailed above and is preferably administered after at least one first cycle with the dose of 10–20 mg/kg (3–4 weeks).

The following table explains the preferred method for a 3-weeks treatment:

| day of the week | Dialysis | Carnitine administration |
|---|---|---|
| Monday | X | X |
| Tuesday | | |
| Wednesday | X | X |
| Thursday | | |
| Friday | X | X |
| Saturday | | |
| Sunday | | |
| Monday | X | X |
| Tuesday | | |
| Wednesday | X | X |
| Thursday | | |
| Friday | X | X |
| Saturday | | |
| Sunday | | |
| Monday | X | X |
| Tuesday | | |
| Wednesday | X | X |
| Thursday | | |
| Friday | X | X |
| Saturday | | |
| Sunday | | |

Wherein X shows a 4-hours dialytic session and the carnitine intravenous administration according to the present invention at the end of the session. 44 hours occur between two subsequent carnitine administrations from Monday to Friday and 68 hours occur between two subsequent carnitine administrations from Friday to Monday.

The maintenance dosage of 5 mg/kg is particularly advantageous, since the patient does not need to continue to receive the attack high dose of 10–20 mg/kg, thus avoiding the always undesirable possible accumulation effect.

The particular embodiment of L-carnitine fumarate is illustrated in the following examples.

EXAMPLE 1

Effect of the Administration of L-carnitine Fumarate on the Perfused Heart

In this example, the low-pressure or low-flow ischaemia model was used, which is a model recognised as valid for cardiac ischaemia (Bolukoglu, H. et al. Am. J. Physiol. 1996: 270; H817–26).

The treatment schedule is illustrated in FIG. 1, in which the letters A–F denote the heart effluent sampling times for the measurement of metabolites. The hearts are removed from the animals and mounted on a Langerdorff appliance. The perfusion medium replacing the blood was a Krebs-Heinsleit standard bicarbonate buffer containing glucose 12 mM as energy source for cardiac metabolism.

After 30 minute perfusion at a pressure of 100 cm of water, ischaemia was induced by reducing the perfusion pressure of the heart to 25 cm of water, thus reducing coronary flow from approximately 2 ml/min to approximately 0.3 ml/min. Reduction of the perfusion pressure gives rise to ischaemia, since the heart will pump the fluid in the low-perfusion area rather than via the coronary bloodstream, supplying the flow to the heart.

This control model was compared with hearts perfused with L-carnitine 10 mM or L-carnitine fumarate 10 mM.

Cardiac function was tested in three different ways.

In the first, the NRM $^{31}$P signal was monitored in real time.

This signal provides the best indication of the energy status of the heart.

In the second, the haemodynamics of the heart was measured by means of a pressure transducer mounted to measure the perfusion pressure. The haemodynamic measurements include heart rate, relative dP/dt (measurement of the contraction force of the heart) and the cardiac contraction amplitude. Coronary flow was also measured as an indicator of the heart's ability to provide oxygen and energy for its own metabolism.

In the third type of test, the metabolites and the enzyme LDH released by the heart were analysed in the effluent. The release of LDH indicates damage to cardiac tissue. The release of metabolites by the heart was tested by means of mass spectrometry coupled with gas chromatography.

The results of the experiments show that the hearts treated with carnitine fumarate have reduced release of LDH; the reserves of high-energy phosphate after 45 minutes of ischaemia are greater in treated hearts, as indicated by the increase in creatine phosphate observed at NMR and the profile of the metabolites released indicates that the treated heart generates less lactate, but more malate. A high lactate level indicates intense anaerobic metabolism and acidosis. The increase in malate indicates that fumarate is metabolised by the heart to yield a system of intermediates of the citric acid cycle favourable to the heart. Haemodynamic function, as indicated by the post-ischemic cardiac contraction amplitude and by coronary flow, is greater in hearts treated with carnitine fumarate.

EXAMPLE 2

The procedures of example 1 were substantially repeated, with the addition of a treatment with carnitine alone as a further control.

Figure 2A:
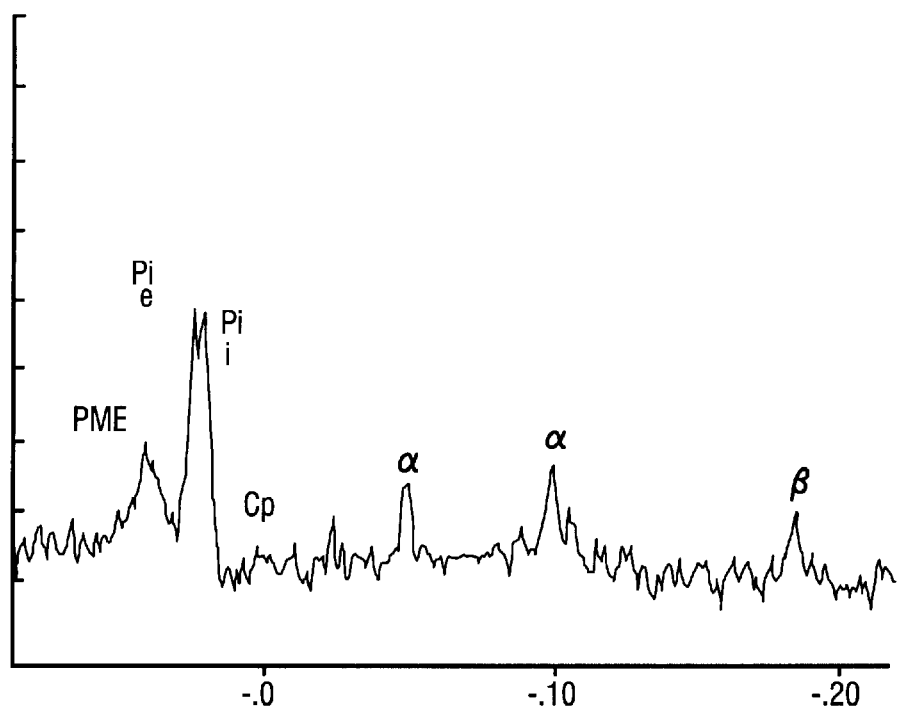
FIG. 2A shows the effect of carnitine on creatine phosphate and ATP.
Figure 2B:
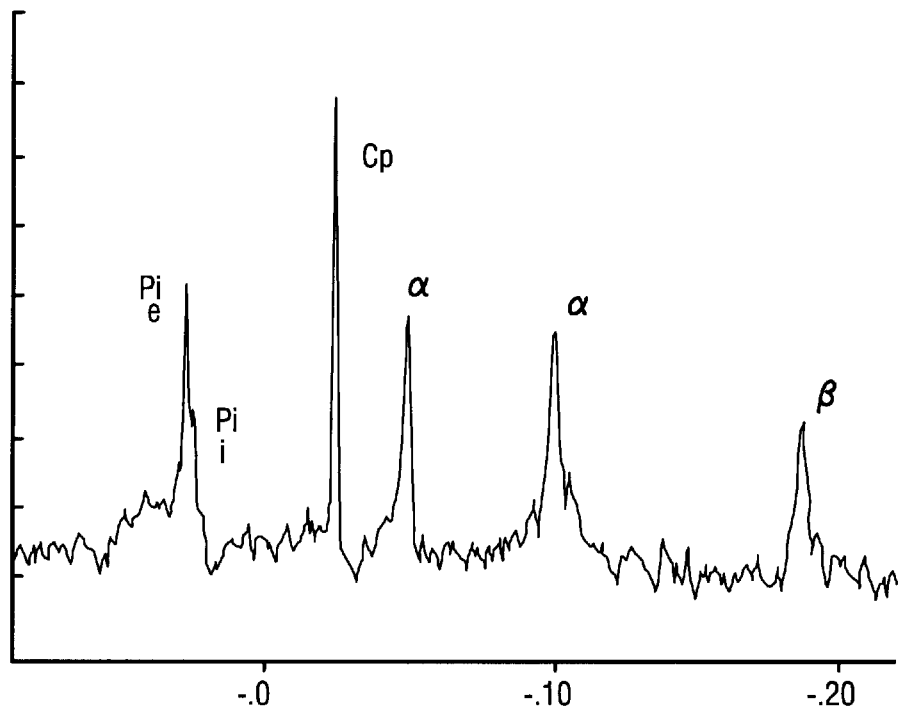
FIG. 2B shows the effect of carnitine fumarate on creatine phosphate and ATP.

The results are given in FIGS. 2–6, where:

FIG. 2 illustrates the effect of carnitine (A) and carnitine fumarate (B) on creatine phosphate and ATP. The data were evaluated after 40 minutes of ischaemia. CP indicates creatine phosphate and α, β and γ denote the phosphate peaks of ATP; as can be seen in part (A) of the figure, the ATP peaks are lacking in the absence of fumarate.

Figure 3A:
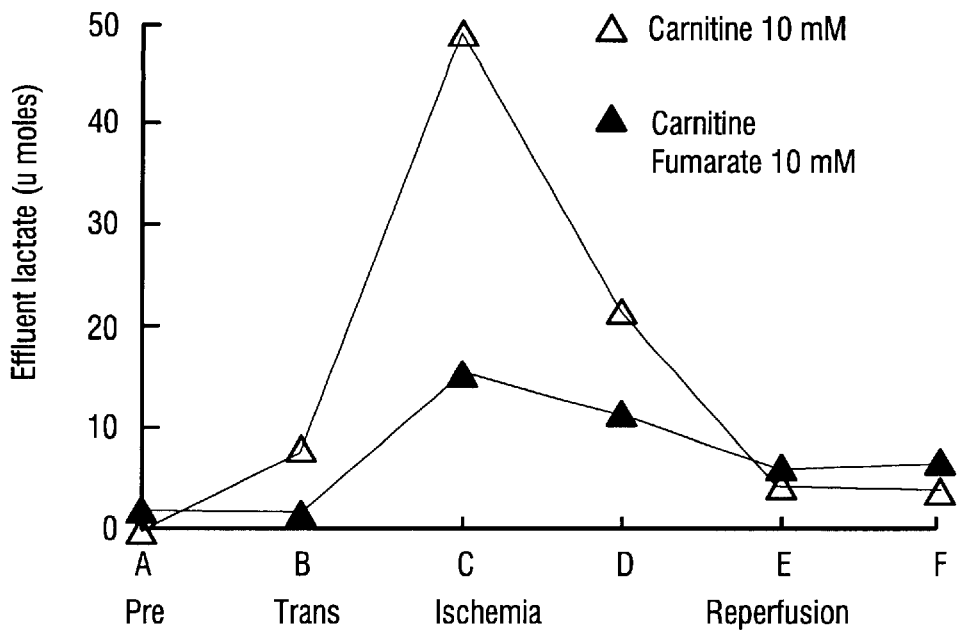
FIG. 3A shows lactate released by the heart, as measured in the effluent.
Figure 3B:
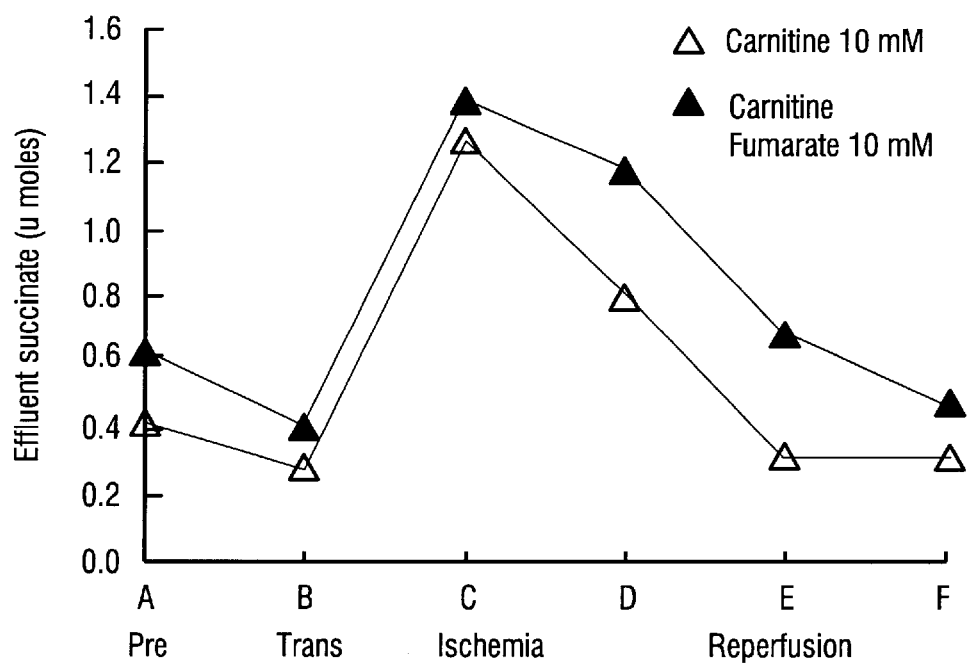
FIG. 3B shows succinate released by the heart, as measured in the effluent.

FIG. 3 shows the comparison between lactate (A) and succinate (B) released by the heart, as measured in the effluent. The lactate reduction indicates the favourable effect of carnitine fumarate. The low amount of succinate as compared to lactate indicates that the generation of ATP as a result of the reduction of fumarate to succinate is not the main source of anaerobic ATP.

Figure 4:
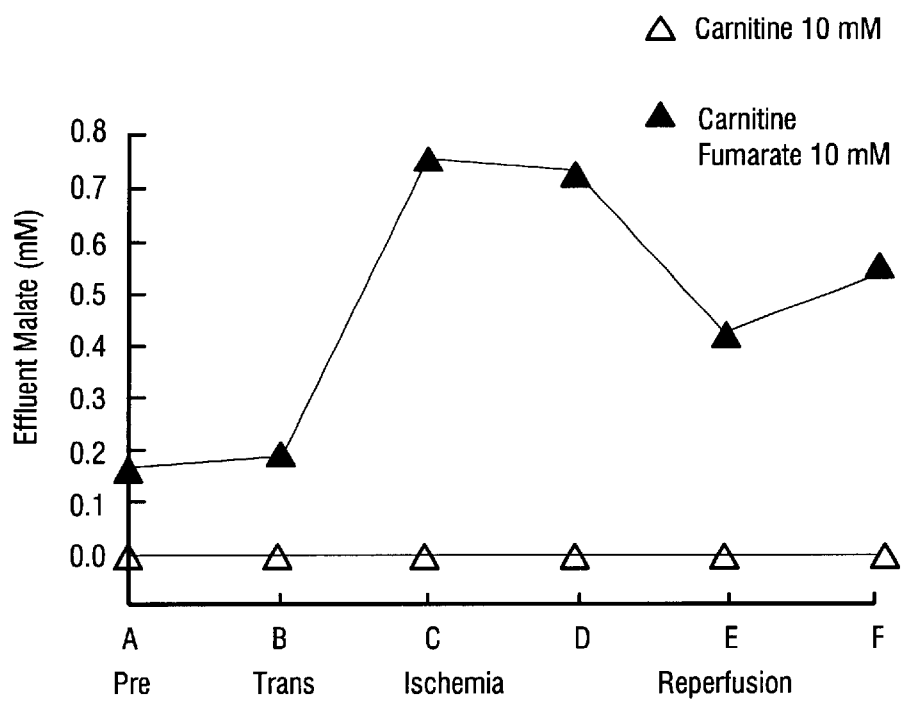
FIG. 4 illustrates the release of malate.

FIG. 4 illustrates the release of malate. The greater malate levels in the treated heart indicate that fumarate enters the cardiac mitochondrion and is metabolised in the TCA cycle.

Figure 5:
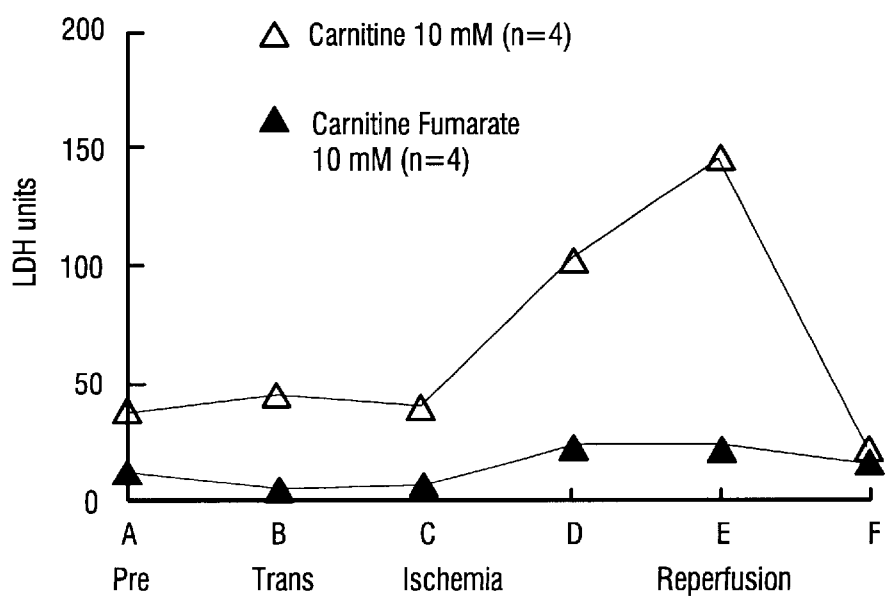
FIG. 5 illustrates the release of LDH.

FIG. 5 illustrates the release of LDH. The greater LDH levels is in controls indicate that carnitine fumarate affords protection against ischemic damage.

Figure 6:
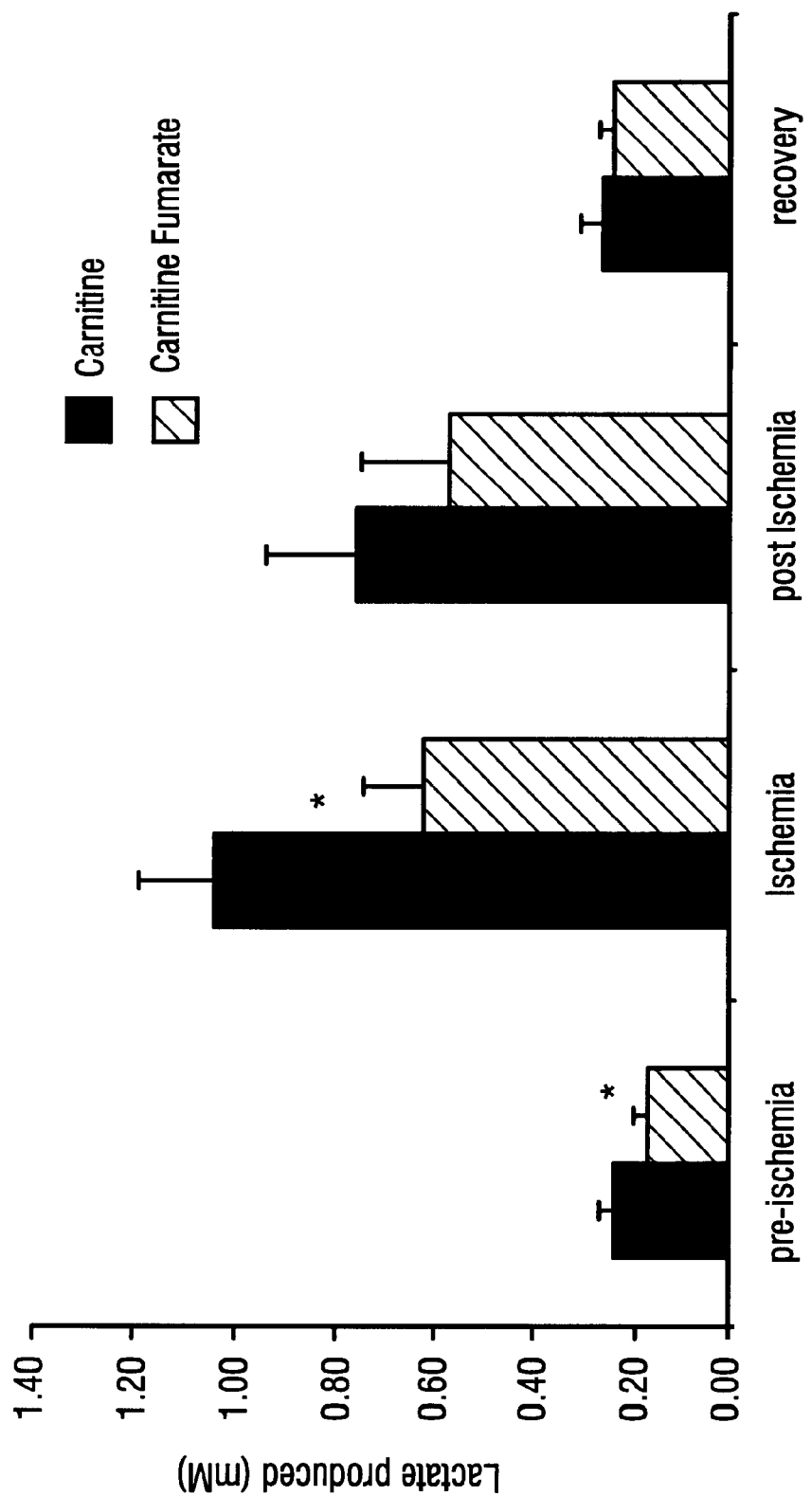
FIG. 6 illustrates the production of lactate.

FIG. 6 illustrates lactate production.

What is claimed is:

1. A method of preventing or treating carnitine deficiency in chronic uremic patients undergoing periodic dialysis comprising administering to a patient into a venous return line after a dialysis session from about 10 to about 20 mg/kg body weight of L-carnitine or of a pharmaceutically acceptable salt thereof and thereafter repeating the administration twice a week every 44 hours, then after 68 hours.

2. The method of claim 1 wherein the treatment is continued for 3–4 weeks, monitoring pre-dialytic levels of carnitine.

3. The method of claim 2, wherein pre-dialytic levels of carnitine are equal or lower than 40–50 $\mu$M.

4. The method of claim 1, wherein a maintenance dosage is provided, administering a dose 5 mg/kg of carnitine.

5. The method of claim 4, wherein the maintenance dosage is repeated twice a week every 44 hours, then after 68 hours.

6. The method of claim 1, wherein carnitine fumarate is the pharmaceutically acceptable salt.

7. The method of claim 6, wherein the patient is affected by hypervolemic heart.

8. The method of claim 6, wherein the patient is affected by diabetes.

9. A method of preventing or treating carnitine deficiency in chronic uremic patients undergoing periodic dialysis comprising administering to a patient into a venous return line after a dialysis session an amount of L-carnitine or of a pharmaceutically acceptable salt thereof effective to restore a level of carnitine in the patient to at least a pre-dialytic level, and thereafter reducing the amount of carnitine administered to a level sufficient to maintain carnitine levels to the pre-dialytic level.

10. A method of preventing or treating carnitine deficiency in chronic uremic patients undergoing periodic dialysis comprising administering to a patient into a venous return line after a dialysis session from about 10 to about 20 mg/kg body weight of carnitine, calculated as L-carnitine, or of a pharmaceutically acceptable salt thereof to restore a level of carnitine in the patient to at least a pre-dialytic level, and thereafter reducing the amount of carnitine administered to a level sufficient to maintain carnitine levels to the pre-dialytic level.

11. The method of claim 10, wherein the treatment to achieve pre-dialytic levels is on a weekly basis repeated twice a week every 44 hours, then after 68 hours.

12. The method of claim 4, wherein the treatment is continued for 3–4 weeks.

13. The method of claim 9 or 10, wherein pre-dialytic levels of carnitine are equal or lower than 40–50 $\mu$M.

14. The method of claim 9 of 10, wherein a maintenance dosage of about 5 mg/kg of carnitine is administered.

15. A method of preventing or treating carnitine deficiency in chronic uremic patients undergoing periodic dialysis comprising administering to a patient at the conclusion of the dialysis an effective amount of L-carnitine or of a pharmaceutically acceptable salt thereof, wherein the administering of L-carnitine or of a pharmaceutically acceptable salt thereof is prompted by the patient demonstrating an initial pre-dialysis plasma carnitine level equal or lower than 40–50 $\mu$M.

16. A method of preventing or treating carnitine deficiency in chronic uremic patients undergoing periodic dialysis comprising administering to a patient into a venous return line after a dialysis session from about 10 to about 20 mg/kg body weight of L-carnitine or of a pharmaceutically acceptable salt thereof and thereafter repeating the administration while monitoring pre-dialysis plasma carnitine levels.

* * * * *